(12) United States Patent
Popp et al.

(10) Patent No.: US 7,682,349 B2
(45) Date of Patent: Mar. 23, 2010

(54) FASTENER ORIENTATION FOR PACKAGED GARMENTS HAVING REFASTENABLE SEAMS

(75) Inventors: Robert L. Popp, Hortonville, WI (US); William M. Lynch, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1894 days.

(21) Appl. No.: 10/632,596

(22) Filed: Aug. 1, 2003

(65) Prior Publication Data

US 2005/0027271 A1    Feb. 3, 2005

(51) Int. Cl.
*A61F 13/15* (2006.01)

(52) U.S. Cl. .................. 604/396; 604/391; 604/386; 604/389; 604/385.03

(58) Field of Classification Search ............ 604/385.01, 604/385.201, 385.03, 396, 386, 389, 391; 206/494, 499, 459.4, 457
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki at al. | |
| 3,849,241 A | 11/1974 | Butin et al. | |
| 4,340,563 A | 7/1982 | Appel et al. | |
| 4,663,220 A | 5/1987 | Wisneski et al. | |
| 4,704,116 A | 11/1987 | Enloe | |
| 4,940,464 A | 7/1990 | Van gompel et al. | |
| 5,046,272 A | 9/1991 | Vogt et al. | |
| 5,104,116 A | 4/1992 | Pohjola | |
| 5,224,405 A | 7/1993 | Pohjola | |
| 5,226,992 A | 7/1993 | Morman | |
| 2002/0117419 A1 | 8/2002 | Tippey et al. | |
| 2002/0123730 A1 | 9/2002 | Popp et al. | |

FOREIGN PATENT DOCUMENTS

| | | |
|---|---|---|
| EP | 0217032 B1 | 2/1992 |
| EP | 1 205 171 A2 | 5/2002 |
| WO | WO 97/49618 | * 12/1997 |
| WO | WO 97/49618 A1 | 12/1997 |

* cited by examiner

*Primary Examiner*—Jacqueline F. Stephens
(74) *Attorney, Agent, or Firm*—H. Michael Kubicki

(57) ABSTRACT

Packaged garments having prefastened, refastenable seams oriented in a certain position can preserve fastener performance. Such refastenable seams are particularly suitable for side seams on pant-like disposable garments. Prior to or during packaging of the garment, the refastenable seams are prefastened and positioned such that any fastening components lie flat in a plane perpendicular to a plane in which front and back panels of the garment lie. When the garment is compressed and packaged, the fastening components remain flat and do not become creased or crushed.

22 Claims, 14 Drawing Sheets

FASTENER ORIENTATION FOR PACKAGED GARMENTS HAVING REFASTENABLE SEAMS

FIELD OF THE INVENTION

This invention is directed to packaged garments having refastenable seams oriented to minimize fastener damage, and to thereby minimize fastener pop-opens during use of the garments.

BACKGROUND OF THE INVENTION

Pant-like disposable garments, such as adult incontinence wear, infant and children's diapers, swim wear and training pants, typically have adhesive or mechanical fasteners on the sides for donning and removal, or else rely on a stretchable waist opening and leg openings to slide on and off the wearer.

Refastenable seams, including, for example, mechanical fasteners such as hook and loop fasteners, have been found to be particularly beneficial when used in conjunction with pant-like disposable garments. Refastenable seams allow for the garment to be easily applied and removed, as well as periodically opened to check for exudates and closed if no exudates are found. For example, pant-like, "pull-on" style disposable garments can have one or more prefastened, refastenable side seams. Such prefastened, refastenable side seams perform at least two useful functions. First, they maintain the garment in a pant-like configuration during donning and removal. Second, they allow for easy inspection of the internal condition of the garment while on the wearer, and allow for refastening if it is not yet necessary to remove the garment. One means of providing a prefastened, refastenable side seam in a pant-like disposable garment is through the use of a mechanical fastener, such as a hook material.

For vending purposes, it is common for pant-like disposable garments to be stacked and placed within compressed packaging. In certain packaging techniques, it is common for the conventional, bonded side seams of the garments to be disposed outside of the stack of garments in a generally uncontrolled manner, rather than being purposefully tucked within the stack of garments. The conventional, bonded side seams of garments stacked in the former manner can press tightly against the wall of the package due to the compressed nature of the package configuration. These conventional, bonded side seams do not use refastenable fasteners and accordingly are not negatively impacted by this compressive force. This untucked and generally uncontrolled packaging technique would be unsuitable for garments having refastenable seams employing mechanical fasteners such as hook components, however, because the hook material can become tightly compressed between the central portion of the stack of garments and the package wall, leading to creasing/crushing of the hook material. Damage to the fastener material may lead to inferior fastener performance (lower peel and/or shear values than uncreased fasteners). Products with severe and/or multiple fastener creases tend to be most apt to pop open during application and wear.

There is a need or desire for pant-like disposable garments having prefastened, refastenable side seams packaged in a way such that the compressive forces exerted by the package walls do not interfere with fastener performance.

SUMMARY OF THE INVENTION

The present invention is directed to packaged garments having refastenable seams. The refastenable seams include fasteners oriented to minimize fastener damage due to compressive forces associated with the packaging.

In one aspect, the present invention relates to a packaged garment defining a waist opening and a leg opening. The garment comprises a front region comprising a front panel and defining a front waist edge, a back region comprising a back panel and defining a back waist edge, and a crotch region connecting the front and back regions. A front side panel extends transversely from a side of the front panel, and a back side panel extends transversely from a side of the back panel. The front side panel is connected to the back side panel to form a prefastened, refastenable seam, and the refastenable seam includes a fastening component. The fastening component lies in a plane approximately perpendicular to a plane in which the front panel lies.

In another aspect, the present invention relates to a packaged garment defining a waist opening and a leg opening. The garment comprises a front region comprising a front panel and defining a front waist edge, a back region comprising a back panel and defining a back waist edge, and a crotch region connecting the front and back regions. A front side panel extends transversely from a side of the front panel, and a back side panel extends transversely from a side of the back panel. The front side panel is connected to the back side panel to form a prefastened, refastenable seam, and the refastenable seam includes a fastening component. The fastening component lies in a plane approximately parallel to a plane in which an adjacent enclosure side wall lies.

In yet another aspect, the present invention relates to a package of prefastened, refastenable garments. The package includes a generally polyhedral enclosure composed of a flexible material surrounding a plurality of prefastened, refastenable garments. The polyhedral enclosure includes a pair of side walls, a pair of end walls, a top wall, and a bottom wall. Each of the plurality of garments includes a front region comprising a front panel and defining a front waist edge, a back region comprising a back panel and defining a back waist edge, and a crotch region connecting the front and back regions. A front side panel extends transversely from a side of the front panel, and a back side panel extends transversely from a side of the back panel. The front side panel is connected to the back side panel to form a prefastened, refastenable seam, and the refastenable seam includes a fastening component. The fastening component lies in a plane approximately perpendicular to a plane in which the front region lies, and in a plane approximately parallel to a plane in which an adjacent side wall lies.

DEFINITIONS

Figure 1:
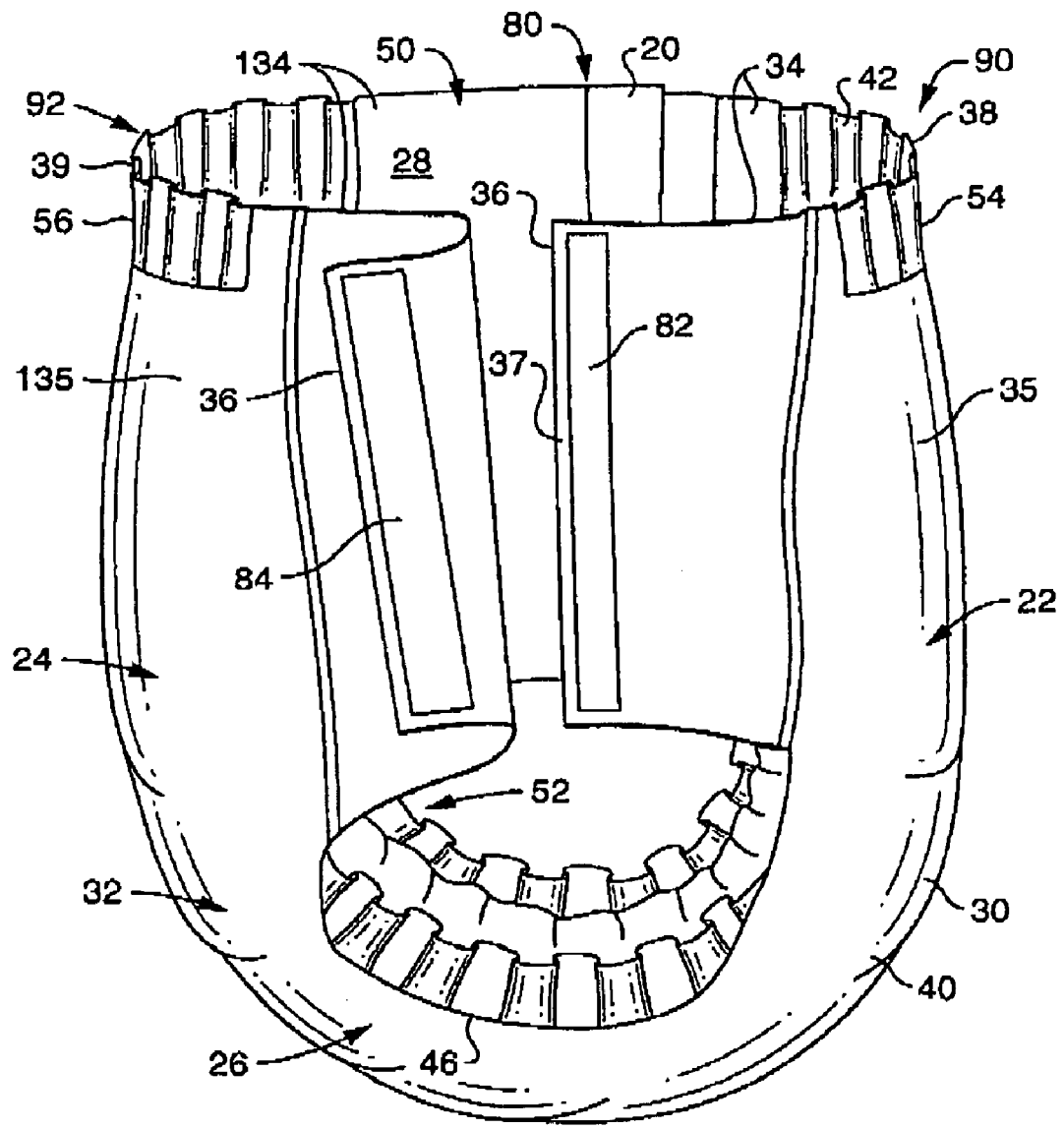
FIG. 1 is a perspective view of a disposable garment having refastenable side seams.

Within the context of this specification, each term or phrase below will include the following meaning or meanings.

"Attached" and variants thereof refer to the joining, adhering, connecting, bonding, or the like, of at least two elements. Two elements will be considered to be attached to one another when they are attached directly to one another or indirectly to one another, such as when each is directly attached to intermediate elements.

"Bonded" and variants thereof refer to the joining, adhering, connecting, attaching, or the like, of at least two elements. Two elements will be considered to be bonded together when they are bonded directly to one another or indirectly to one another, such as when each is directly bonded to intermediate elements.

"Connect" and variants thereof refer to the attaching, joining, adhering, bonding, or the like, of at least two elements. Two elements will be considered to be connected to one another when they are connected directly to one another or indirectly to one another, such as when each is directly connected to intermediate elements.

"Elastomeric" and "elastic" refer to that property of a material or composite by virtue of which it tends to recover its original size and shape after removal of a force causing a deformation. It is generally preferred that the elastomeric material or composite be capable of being elongated by at least 50 percent, more preferably by at least 300 percent, of its relaxed length and recover, upon release of an applied force, at least 50 percent of its elongation.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 2:
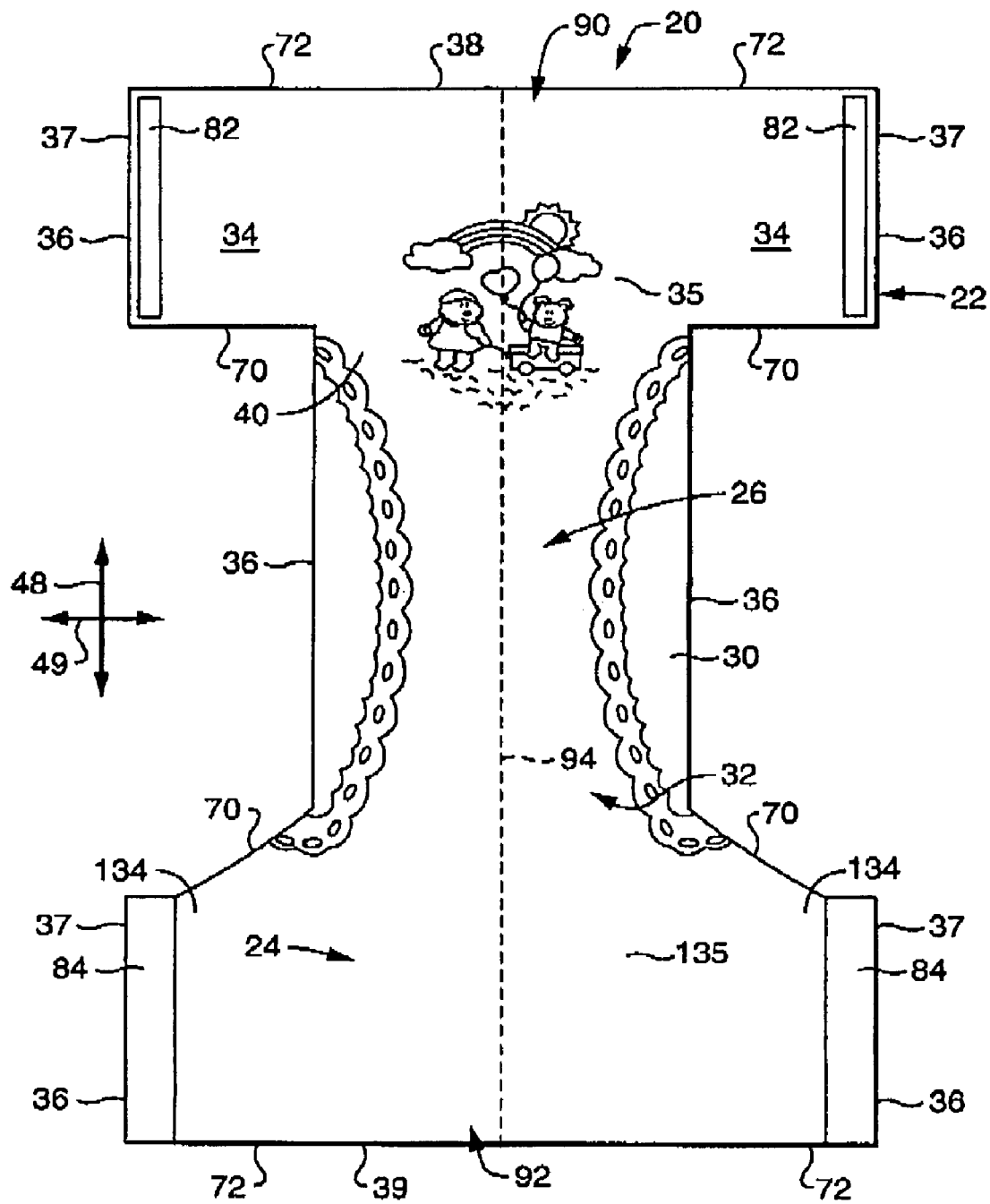
FIG. 2 is a plan view of a disposable garment in a stretched flat state showing the surface of the garment that faces away from the wearer when the garment is worn.
Figure 3:
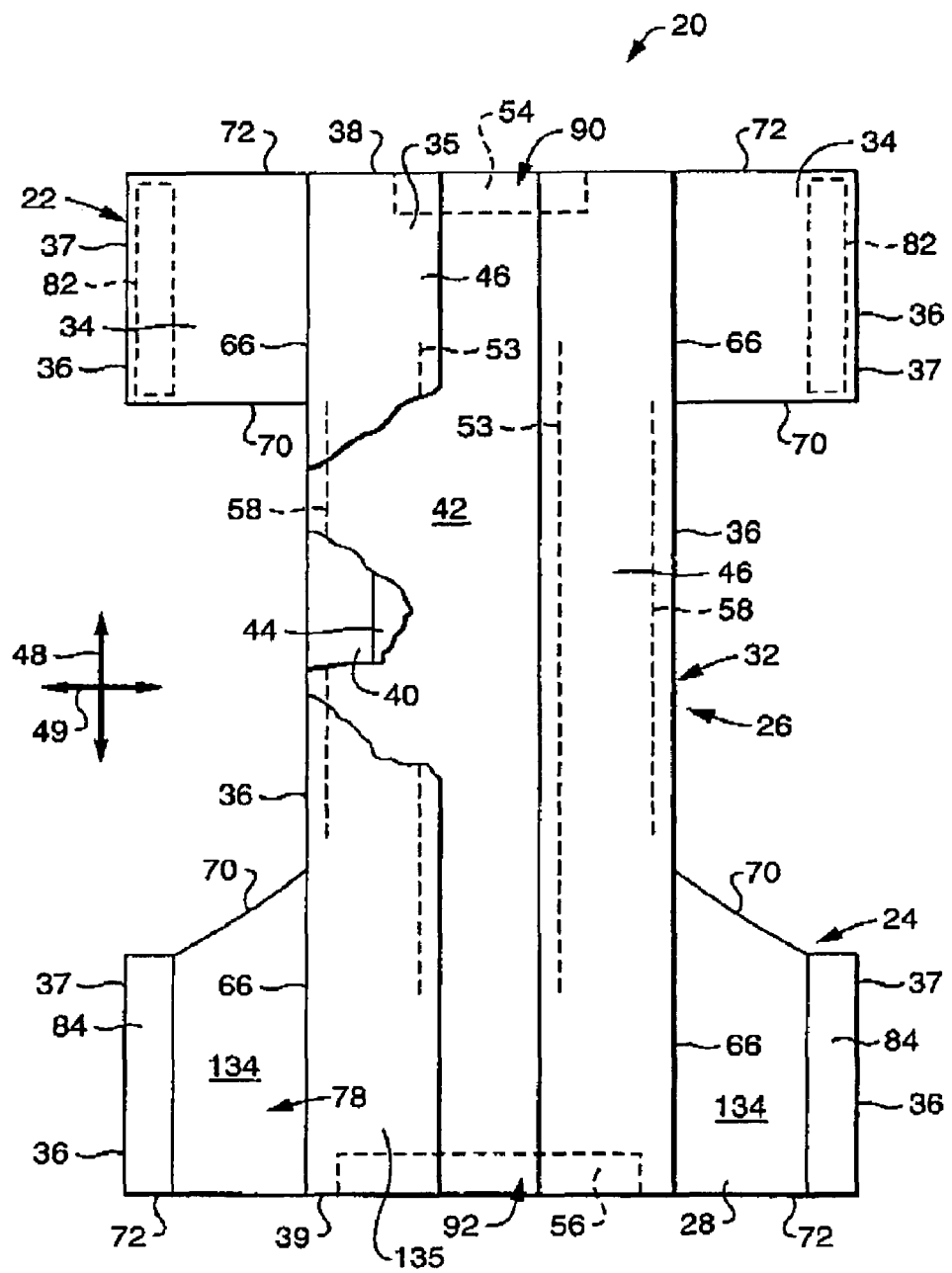
FIG. 3 is a plan view of a disposable garment in a stretched flat state showing the surface of the garment that faces the wearer when the garment is worn, and with portions cut away to show the underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is generally longer in the longitudinal direction than in the transverse direction, although products longer in the transverse direction are also possible.

"Longitudinal midline" refers to a line, either real or imaginary, that runs along the longitudinal length of the chassis of an absorbent garment and bisects the chassis into two halves of equal transverse width.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently attached, "permanently bonded," or "permanently connected" refers to the joining, adhering, connecting, attaching, bonding, or the like, of two elements of an absorbent garment such that the elements tend to be and remain attached during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture. The refastenable elements can be attached, separated and reattached for at least one cycle, suitably for at least 5 cycles, or suitably for at least 10 cycles.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Self-engaging fastener" refers to a fastening component that can engage with another fastening component having the same structure.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802, 817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 250% of its initial length, desirably to at least 300% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a nonsoftened condition when cooled to room temperature.

These terms may be defined with additional language in the remaining portions of the specification.

Detailed Description of the Presently Preferred Embodiments

The present invention is directed to garments having refastenable seams which include a fastener oriented so as to avoid fastener damage associated with packaging. Orienting the fastening components perpendicular to the front and/or back panels of the pant, and orienting the fastening components parallel to the adjacent enclosure wall reduces the likelihood of creases occurring in the fastening components, thereby preserving the available fastener seam strength and making the fasteners less likely to disengage during product application and wear.

The principles of the present invention can be incorporated into any suitable disposable garment having a prefastened and refastenable seam. Examples of such suitable garments include diapers, training pants, incontinence products, other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Referring to FIG. 1, a disposable absorbent article, such as a training pant 20, is illustrated in a partially fastened condition. The training pant 20 includes two refastenable seams 80, each extending from a waist opening 50 to one of two leg openings 52 on opposing sides of the garment 20. Each seam 80 includes a fastening component 82 and a mating fastening component 84. Either the fastening component 82 or the mating fastening component 84, or both, can be, but need not be, a resilient fastening component. The term "resilient" as used herein refers to an interlocking material having a predetermined shape, and which has the ability to resume that predetermined shape after being engaged and disengaged from a mating, complementary interlocking material. The resilient fastener may be deformed under great stress, such as during compression associated with packaging operations, particularly when the fastening component does not lie flat in a plane perpendicular to an applied compressive force. Resilient fastening components are typically formed from resilient material and have a backing and a plurality of engaging elements that project from the backing. An example of a suitable resilient fastening component is a hook type fastener that can repeatedly be engaged with and released from a loop type fastener. The terms "fastener" and "fastening component" are used interchangeably herein.

It has been found that fastener performance can be compromised when a resilient fastening component in a refastenable seam is creased during processing or compression in preparation for or during packaging. Usually, creases in fastening components formed during packaging and storage do not completely unfold or disappear during subsequent use of the garment. A crease or creases in a fastener hook component can deform individual hooks or the underlying material. The result of either deformation can be reduced engagement ability due either to deadened hooks or to spacing between hooks and loop material that prevent hooks from engaging in the loop material. When any hooks on a hook component are deadened, the engageable area of the hook component is reduced. As a result, a creased fastener tends to possess lower peel and/or shear values than uncreased fasteners. Products with severe and/or multiple fastener creases tend to be most apt to pop open during application and wear due to a greater number of deadened engagement elements. Creases can also hinder performance of fastener loop materials by flattening some of the loops, and by spacing some of the loops farther away from the hook material.

The orientation, relative to other portions of the garment or to the surrounding packaging material, of the fastening components 82 of the present invention in preparation for and/or during packaging prevents fastener creases from occurring, thus preserving the available fastener seam strength and making fasteners, such as hook and loop fasteners, less likely to disengage during product application and wear. A detailed description of the orientation of the fastening components 82 for packaged garments follows a description of the garment 20 below.

The following descriptions and drawings are representative examples only, and are not intended to delimit the scope of the invention.

Referring again to FIG. 1, the training pant 20 includes an absorbent chassis 32 defining a front region 22, a back region 24, and a crotch region 26 interconnecting the front and back regions. The training pant 20 also includes an inner, body-facing surface 28 which is configured to contact or face toward the wearer's body, and an outer, clothing-facing surface 30 opposite the body-facing surface which is configured to contact or face toward the wearer's clothing. With additional reference to FIGS. 2 and 3, the absorbent chassis 32 also defines a pair of transversely opposed distal edges 36 and a pair of longitudinally opposed waist edges, which are designated front waist edge 38 and back waist edge 39. The front region 22 is contiguous with the front waist edge 38, and the back region 24 is contiguous with the back waist edge 39. The chassis 32 also includes a pair of transversely opposed front side panels 34 and a pair of transversely opposed back side panels 134. The front and back side panels 34, 134 are formed along the distal edges 36 of the chassis and can either be integrally formed with the chassis, as shown in FIG. 2, or can each include at least one separate element permanently attached to the chassis, as shown in FIGS. 1 and 3. The side panels 34 and 134 each define side panel distal edges 37. For reference, arrows 48 and 49 depicting the orientation of the longitudinal axis and the transverse axis, respectively, of the training pant 20 are illustrated in FIGS. 2 and 3.

The illustrated absorbent chassis 32 can include an outer cover 40, a bodyside liner 42 which is connected to the outer cover in a superposed relation, an absorbent assembly 44 which is located between the outer cover 40 and the bodyside liner 42, and a pair of containment flaps 46, as shown in FIG. 3.

The front side panels 34 shown in FIGS. 5-13 each include fastening components incorporated therein, either in the form of separate fastening components 82, as shown in FIGS. 5-13, or in the form of fastening material forming at least a portion of the side panels 34, such that one fastening component on each side panel 34 can be releasably engaged with a mating fastening component incorporated into each back side panel 134. Similarly, the mating fastening components can be in the form of either separate mating fastening components 84, as shown in FIGS. 5, 7, 9, 11, and 13, or in the form of mating fastening material forming at least a portion of the side panels 134. In various embodiments, either the entire outer cover 40 or the entire body side liner 42 or the front side panels 34 or the back side panels 134 can be made of a fastening material or a mating fastening material. The entire garment may be stretchable in one or more directions, and may be elastomeric in one or more directions.

With the training pant 20 in the fastened position, as partially illustrated in FIG. 1, the front and back regions 22 and 24 are joined together to define a three-dimensional pant configuration having a waist opening 50 and a pair of leg openings 52. The phrases "front region," "back region," "front panel," "back panel," "front waist region," "back waist region," "front waist edge," and "back waist edge" as used herein merely refer to a particular region of the pant, and are not intended to limit where a particular region of the pant must be positioned on a wearer. For instance, the front region 22 as that phrase is used herein can include the portion of the training pant 20 which, when worn, is positioned on either the front or back of the wearer. Similarly, the back region 24 as that phrase is used herein can include the portion of the training pant which, when worn, is positioned on either the front or back of the wearer. The same alternative character applies to the other phrases just listed. The crotch region 26 of the training pant 20 includes the portion of the training pant which, when worn, is positioned between the legs of the wearer and covers the lower torso of the wearer. The front and back side panels 34, 134 include the portions of the training pant 20 which, when worn, are positioned on the hips of the wearer.

As representatively shown in FIG. 3, the front region 22 of the absorbent chassis 32 includes the transversely opposed front side panels 34 and a front panel 35 positioned between and interconnecting the side panels, along with a front waist elastic member 54 and any other connected components. A front waist region 90 is a region of the front panel 35 along the front waist edge 38. The back region 24 of the absorbent chassis 32 includes the transversely opposed back side panels 134 and a back panel 135 positioned between and interconnecting the side panels, as well as a rear waist elastic member 56 and any other connected components. A back waist region 92 is a region of the back panel 135 along the back waist edge 39. The waist edges 38 and 39 of the absorbent chassis 32 are configured to encircle the waist of the wearer when worn and provide the waist opening 50 which defines a waist perimeter dimension. Portions of the transversely opposed distal edges 36 of the chassis 32 in the crotch region 26, along with leg end edges 70 of the side panels 34 and 134, generally define the leg openings 52.

The absorbent chassis 32 is configured to contain and/or absorb any body exudates discharged from the wearer. For example, the absorbent chassis 32 desirably, although not necessarily, includes the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed distal edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39 as well as over waist edges 72 of the side panels 34, 134, and can extend over part or all of the waist edges. The leg elastic members 58 can be operatively joined to the outer cover 40 and/or bodyside liner 42 while longitudinally aligned along the distal edges 36 and positioned in the crotch region 26 of the chassis 32.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together thermally, ultrasonically, by a laminate adhesive, or by any other suitable methods known in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture and/or mating fastening component qualities. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. As mentioned, the bodyside liner 42 and/or the outer cover 40 can be made of a fastening component material or a mating fastening component material to eliminate the need for separately attached mating fastening components.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Uniqema, Inc., a division of ICI of New Castle, Del., and GLUCOPON® 220UP from Cognis Corp. of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) is positioned between the outer cover 40 and the bodyside liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. High absorbency material can be provided in any form known in the art, including but not limited to particles, fibers, foams and films.

In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 0 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue, nonwoven, woven, composite, or other material that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34, 134 disposed on each side of the absorbent chassis 32. These transversely opposed front side panels 34 and transversely opposed back side panels 134 can be permanently bonded to the front panel 35 and back panel 135 in the respective front and back regions 22, 24 along attachment lines 66, and are releasably attached to one another. The side panels 34, 134 may be permanently attached to panels 35, 135 using attachment means known to those skilled in the art such as adhesive, thermal or ultrasonic bonding. As mentioned, the side panels 34, 134 can also be formed as continuous extensions of the front and back panels 35, 135.

As shown in FIGS. 5-13, the fastening components 82 can be permanently bonded to either the inner, body-facing surface 28 or the outer, clothing-facing surface 30 of each front side panel 34 adjacent the distal edge 37 of each front side panel, and the mating fastening components 84 can be permanently bonded to either the inner, body-facing surface 28 or the outer, clothing-facing surface 30 of each back side panel 134 adjacent the distal edge 37 of each back side panel, or either the inner surface 28 or the outer surface 30 of the chassis 32 can include a fastening material or a mating fastening material. In addition, the positions of the fastening components 82 and mating fastening components 84 may be reversed. The fastening components 82 and the mating fastening components 84 may be attached to the side panels 34, 134 and the chassis 32 using attachment means known to those skilled in the art such as adhesive, thermal or ultrasonic bonding.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. In yet another embodiment, half of the fastening components 82 and half of the mating fastening components 84 can include hook type fasteners, while half of the fastening components 82 and half of the mating fastening components 84 can include loop type fasteners. In still another embodiment, each of the fastening components 82 and the mating fastening components 84 include self-engaging fasteners. The fastening components 82 and the mating fastening components 84 are desirably rectangular, although they may alternatively be square, round, oval, curved, discontinuous such as multiple fasteners, or any other suitable shape. The fastening components 82 and mating fastening components 84 may or may not be parallel to a longitudinal midline 94 of the garment 20.

In another embodiment, the nonwoven web in the outer cover 40 can be constructed of a material that is suitable for use as a loop-type fastening material, thereby eliminating the need for separate loop-type fastening components 82 or 84, and the fastening components 82 or 84 on the side panels 34 or 134 can be hook-type fastening components. In yet another embodiment, the nonwoven web in the bodyside liner 42 can be constructed of a material that is suitable for use as a loop-type fastening material, thereby eliminating the need for separate loop-type fastening components 82 or 84, and the fastening components 82 or 84 on the side panels 34 or 134 can be hook-type fastening components. In still another embodiment, an inner or outer surface of either the front side panels 34 or the back side panels 134 can include a loop-type fastening material, thereby eliminating the need for separate loop type fastening components 82 or 84.

Loop type fasteners typically include a fabric or material having a base or backing structure and a plurality of loop members extending upwardly from at least one surface of the backing structure. The loop material may include woven or nonwoven materials. The loop material can be formed of any suitable material, such as acrylic, nylon, polyester, polypropylene, or polyethylene, and can be formed by methods such as warp knitting, stitch bonding, needle punching, or spunbound, meltblown, or bonded-carded processes as are known in the art. Additionally, loop material can be non-stretchable or stretchable, and can be elastomeric. One suitable loop material is available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. Suitable hook material can be molded or extruded of nylon, polypropylene or another suitable material. Suitable single-sided hook materials for the fastening components 82 or the mating fastening components 84 are available from commercial vendors such as Velcro Industries B.V., Amsterdam, Netherlands or affiliates thereof, and are identified as Velcro HTH-829 with a unidirectional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

In particular embodiments for improved fit and appearance, the side panels 34, 134 desirably have an average length dimension measured parallel to the longitudinal axis 48 that is about 10 percent or greater, more particularly about 15 percent or greater, and still more particularly about 20 percent or greater, of the overall length dimension of the absorbent article, also measured parallel to the longitudinal axis 48. For example, in training pants having an overall length dimension of about 54 centimeters, the side panels 34, 134 desirably have an average length dimension of about 10 centimeters or greater, such as about 15 centimeters. A waist end edge 72 of each side panel 34, 134 can suitably be relatively straight across in the transverse direction while the leg end edge 70 of each side panel 34, 134 can suitably have a curvature, as shown in FIGS. 2 and 3 with respect to side panels 134, to allow the leg opening 52 to conform about a wearer's leg.

Each of the side panels 34, 134 can include one or more individual, distinct pieces of material in addition to the fastening components 82, 84, as shown in FIG. 3. In particular embodiments, for example, each side panel 34, 134 can include first and second side panel portions that are joined at a seam, with at least one of the portions including an elastomeric material. The side panels 34, 134 can include an elastic material capable of stretching in a direction generally parallel to the transverse axis 49 of the training pant 20, generally parallel to a longitudinal axis 48 of the training pant 20, or both. The front side panels 34 and the back side panels 134 can be of equal widths or of different widths in the transverse direction.

Suitable elastic materials, as well as one described process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

The desired orientation of the refastenable seams 80 before and/or during compression and/or packaging requires, first, that the seams be prefastened, i.e., the fastening component 82 is releasably attached to the mating fastening component 84, and second, that each fastening component, whether attached to the front side panels 34 or the back side panels 134, be situated in a plane approximately perpendicular to a plane in which the front panel 35 lies. Furthermore, the front panel 35 and the back panel 135 lie in parallel planes; thus, the planes in which the fastening components lie are also approximately perpendicular to the plane in which the back panel 135 lies. The side panels 34, 134 must be fastened and purposefully positioned and/or folded in order to achieve this orientation. As used herein, the "plane" in which a component lies is the plane which includes the components largest two dimensions. For example, the plane in which a fastening component "lies" is the plane which includes the length and width dimensions of the fastening component, both of which are greater than the thickness of the fastening component. "Approximately perpendicular" means perpendicular or nearly perpendicular. Similarly, "approximately parallel" means parallel or nearly parallel.

FIGS. 5-12 show exemplary embodiments of packaged positions 21 of pant-like garments 20 having prefastened, refastenable seams 80. The phrase "packaged position" refers to the placement and configuration of various components of the garment with respect to other components of that garment or to a surrounding packaging material when the garment is in a package. Each garment 20 includes a front region 22 having a front panel 35 and two front side panels 34. Each garment also includes a back region 24 having a back panel 135 and two back side panels 134. The side panels shown in FIGS. 2 and 4-16 are integral with the front and back panels 35 and 135, though they could also be separate components bonded to the front and back panels. The front panels 35 are connected to the back panels 135 to form refastenable seams 80, thus placing the garment 20 in a three-dimensional, pant-like configuration. Each refastenable seam 80 includes at least one fastening component 82, which may or may not be resilient. In each of the embodiments illustrated, the garment 20 is in a packaged position 21 such that the side panels 34 and 134 and the refastenable seam 80 are not located between the front and back panels 35 and 135, but instead are disposed transversely outward from the front and back panels 35 and 135. Moreover, each resilient fastening component 82 lies in a plane which is perpendicular to a plane in which the front panel 35 lies.

Figure 4:
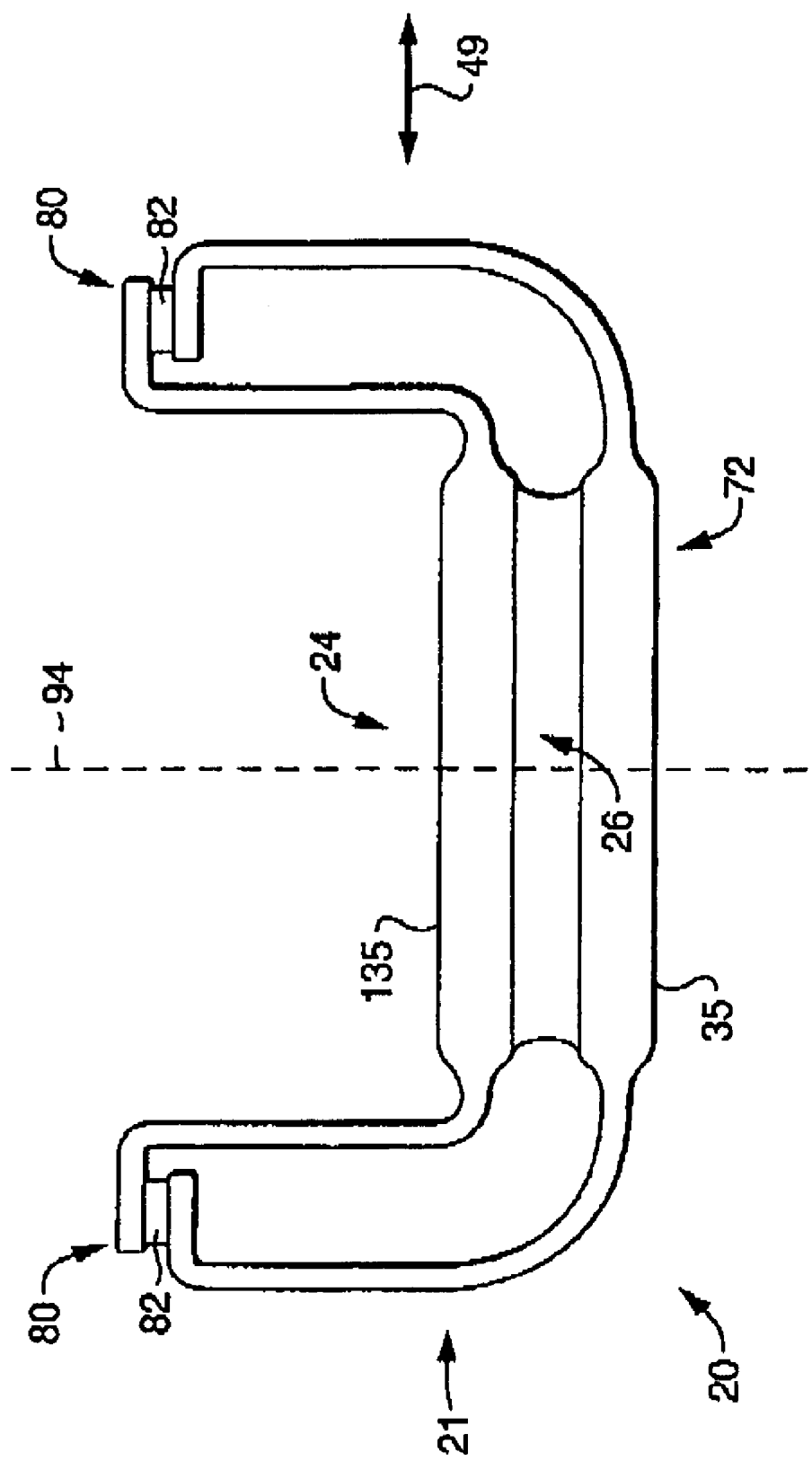
FIG. 4 is a top view of a waist region of a disposable garment having prefastened, refastenable side seams positioned such that they may be subject to damage during packaging.
Figure 5:
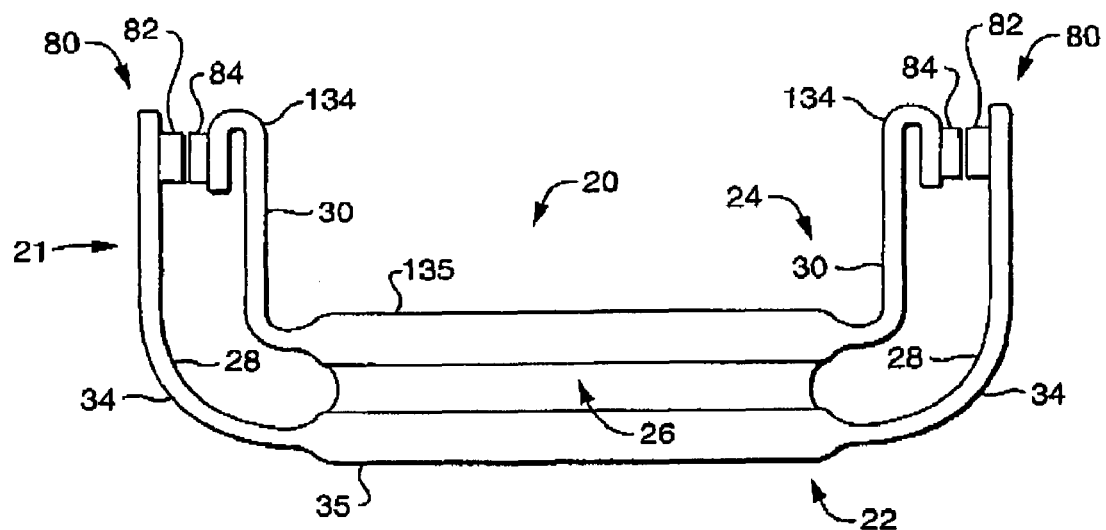
FIG. 5 is a top view of a waist region of a disposable garment having prefastened, refastenable side seams in one embodiment of the invention.
Figure 6:
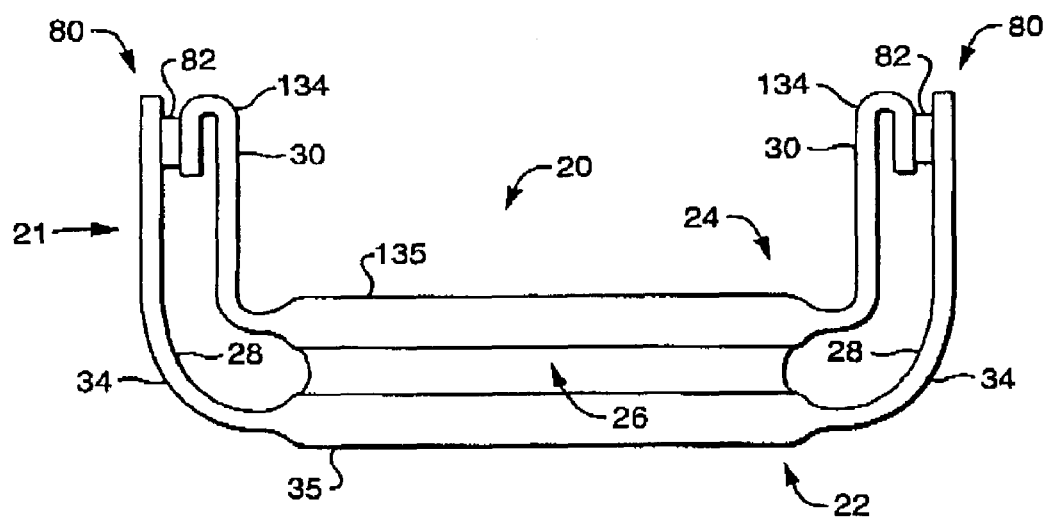
FIG. 6 is a top view of a waist region of a disposable garment having prefastened, refastenable side seams in another embodiment of the invention.
Figure 7:
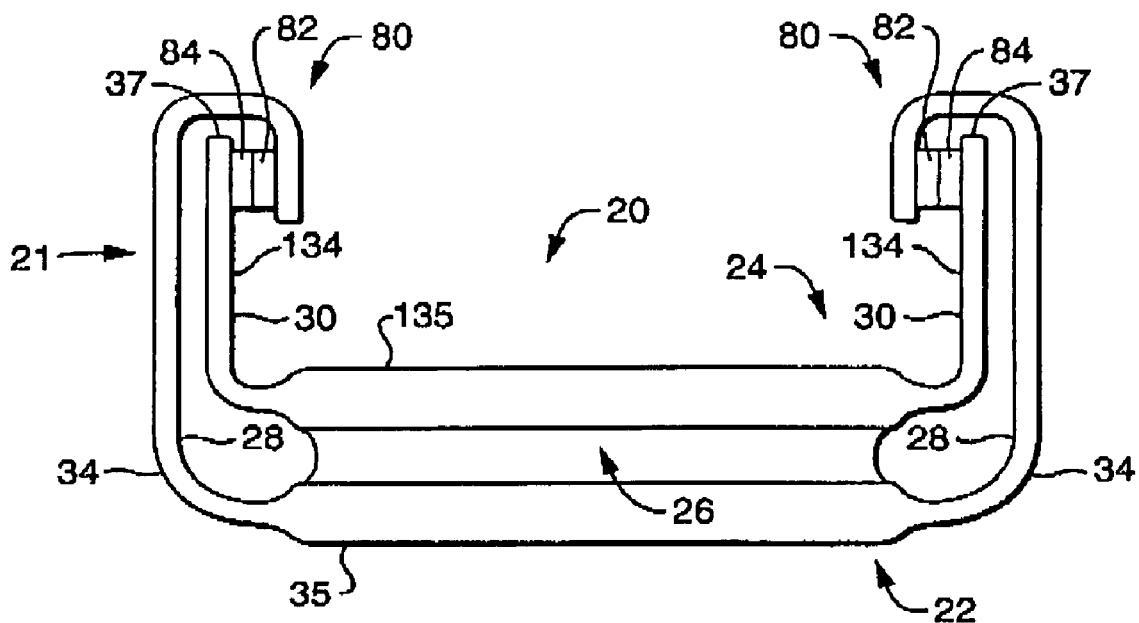
FIG. 7 is a top view of a waist region of a disposable garment having prefastened, refastenable side seams in another embodiment of the present invention.
Figure 8:
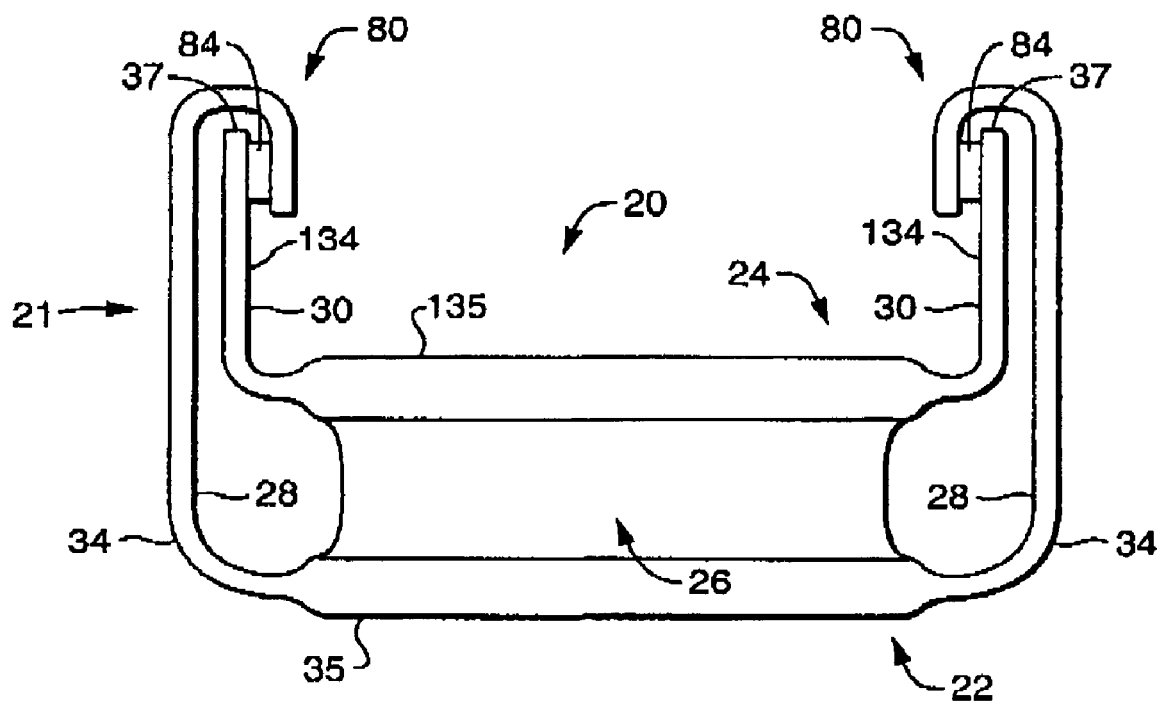
FIG. 8 is a top view of a waist region of a disposable garment having prefastened, refastenable side seams in another embodiment of the present invention.
Figure 9:
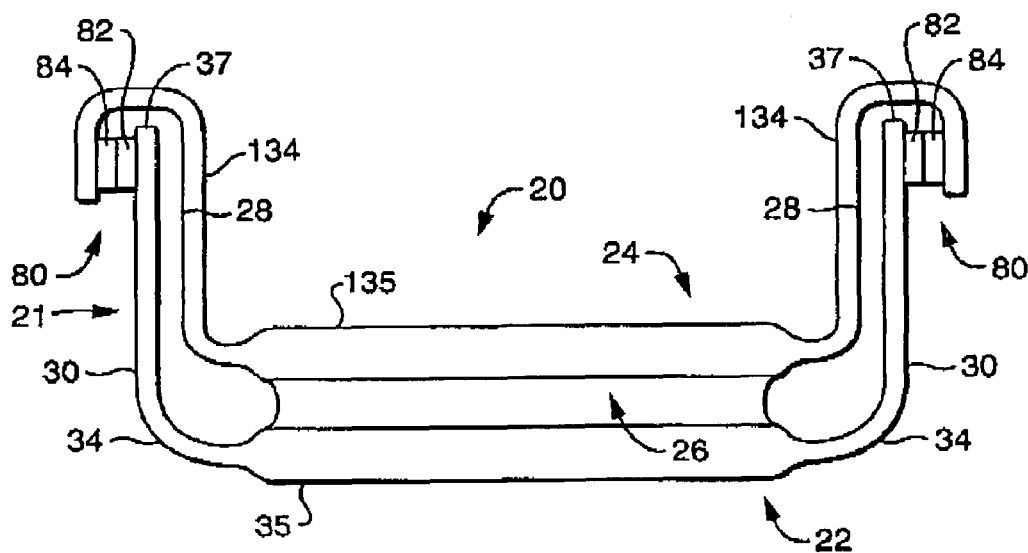
FIG. 9 is a top view of a waist region of a disposable garment having prefastened, refastenable side seams in another embodiment of the present invention.
Figure 10:
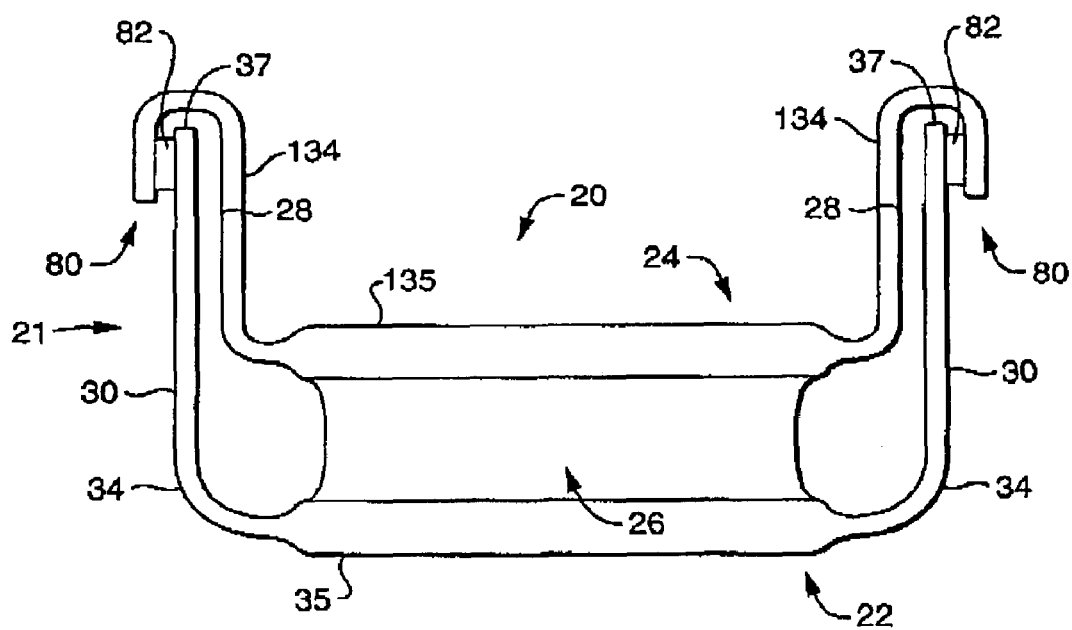
FIG. 10 is a top view of a waist region of a disposable garment having prefastened, refastenable side seams in another embodiment of the present invention.
Figure 11:
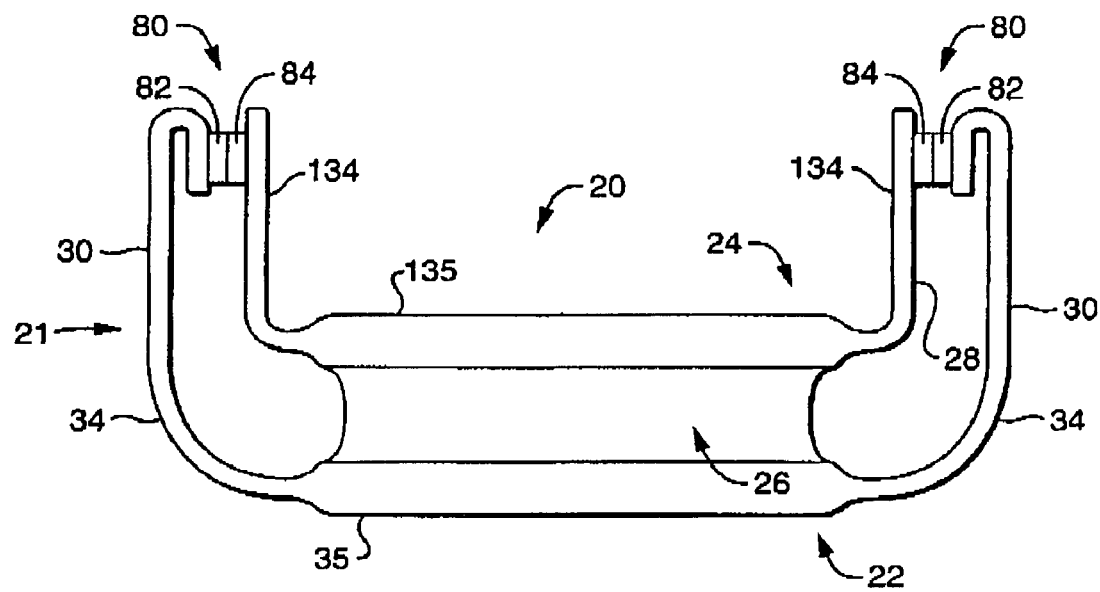
FIG. 11 is a top view of a waist region of a disposable garment having prefastened, refastenable side seams in another embodiment of the present invention.
Figure 12:
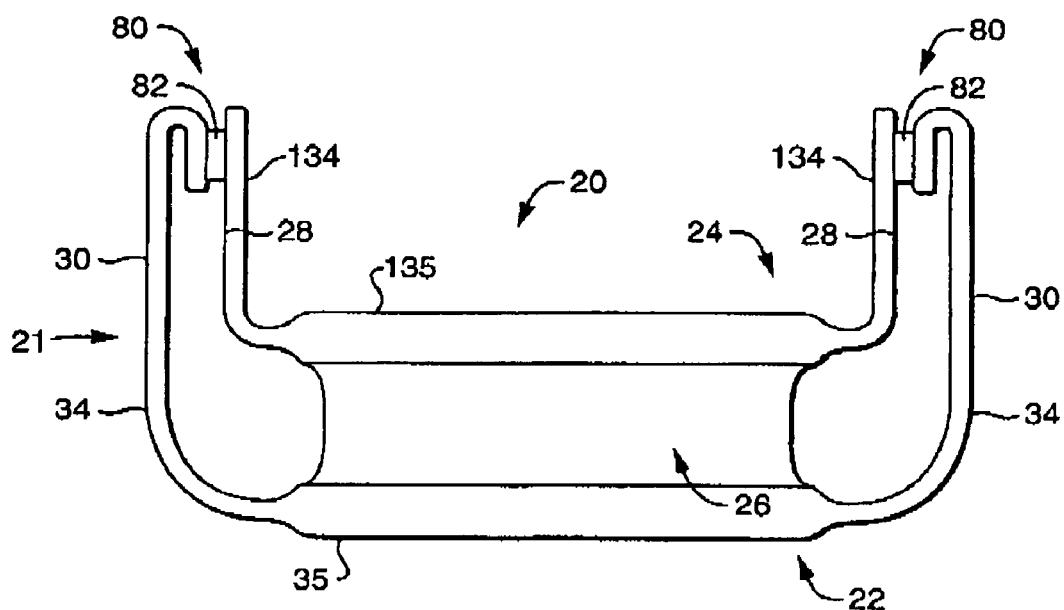
FIG. 12 is a top view of a waist region of a disposable garment having prefastened, refastenable side seams in another embodiment of the present invention.

FIG. 4 illustrates an example of a packaged position 21 which can result in damage to the resilient fastener 82. In this configuration, the inward compressive force of a surrounding packaging equipment or packaging material, pressing toward the longitudinal midline 94 of the garment 20, can crease, deform, or otherwise damage the fastening component 82, resulting in the problems previously discussed. For example, the side wall of a flexible bag (not shown in FIG. 4) can press in a transverse direction 49 toward the longitudinal midline 94 of the garment 20, potentially causing damage to the fastening component 82 oriented as in FIG. 4.

In the representative embodiments shown in FIGS. 5-8, each refastenable seam 80 is formed by connecting a body-facing surface 28 of each front side panel 34 to a clothing-facing surface 30 of each back side panel 134. In the packaged position shown in FIGS. 5 and 6, each back side panel 134 is folded 180 degrees near the seam 80. In the packaged positions shown in FIGS. 7 and 8, each front side panel is folded 180 degrees near the seam 80, such that each front side panel is folded over a distal edge 37 of each back side panel 134. These folds help to properly position the resilient fastening components 82 such that damage to the fastening components associated with packaging can be avoided.

In the representative embodiments shown in FIGS. 9-12, each refastenable seam 80 is formed by connecting a clothing-facing surface 30 of each front side panel 34 to a body-facing surface 28 of each back side panel 134. In the packaged positions shown in FIGS. 9 and 10, each back side panel 134 is folded 180 degrees near the seam 80, such that each back side panel is folded over a distal edge 37 of each front side panel 34. In the packaged position shown in FIGS. 11 and 12, each front side panel 34 is folded 180 degrees near the seam 80. Again, these folds help to properly position the resilient fastening components 82 such that damage to the fastening components during packaging can be avoided.

FIGS. 5, 7, 9, and 11 illustrate the use of fastening components 82 and complementary mating fastening components 84. In each of these Figures, the resilient fastening components 82 are shown as being bonded to the front side panels 34, and the mating fastening components are shown as being permanently secured to the back side panels 134. However, as indicated earlier, the positions of the fastening components can be reversed. Thus, the resilient fastening components 34 could be permanently secured to the back side panels 134, and the mating fastening components could be permanently secured to the front side panels 34. Further, as stated before, the mating fastening components 84 may or may not be resilient.

FIGS. 6, 8, 10, and 12 are similar to FIGS. 5, 7, 9, and 11, respectively, except that in the former set of Figures, no separate mating fastening component is employed. Instead, the resilient fastening components 82 directly engage an engageable surface of the opposing side panel to form the refastenable seams 80. The resilient fastening component 82 can be permanently attached to any of the side panels to provide the pant-like garment 20. For instance, the resilient fastening component 82 can be permanently secured to each front side panel 34, and can engage the surface of the each back side panel 134. Alternatively, the resilient fastening component 82 can be permanently secured to each back side panel 134, and can engage the surface of each front side panel 34. In yet another alternative, one resilient fastening component 82 may be permanently secured to one front side panel 34 on a garment, and another resilient fastening component may be permanently secured to a back side panel 134 diagonally (both longitudinally and transversely) opposite the one front side panel 34.

Figure 13:
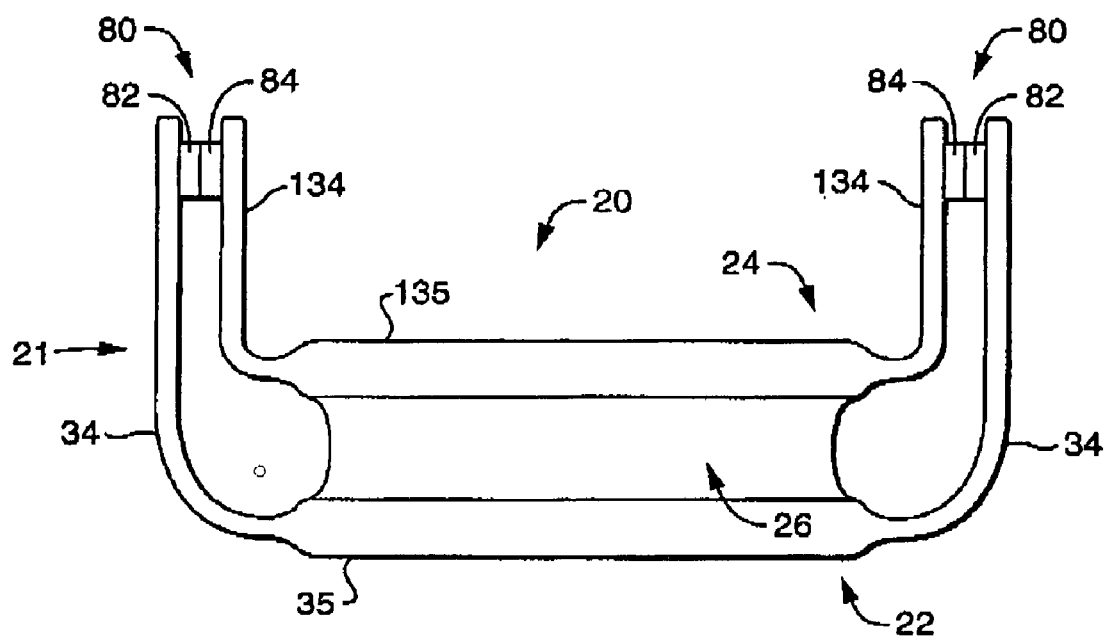
FIG. 13 is a top view of a waist region of a disposable garment having prefastened, refastenable side seams in another embodiment of the present invention.

Each of the refastenable seams 80 shown in FIGS. 5-12 is a "lap" seam, meaning that the front and back side panels 34 and 134 are connected to each other in an overlapping configuration, such that the body-facing surface of one side panel is connected to the clothing-facing surface of the longitudinally opposite side panel, or vice versa. Such a lap seam normally experiences a shearing stress during use of the garment. FIG. 13 representatively illustrates a garment 20 having refastenable seams 80 in a "fin" seam configuration, meaning that the front and back side panels 34 and 134 are connected to each other in a face-to-face configuration, such that the body-facing surface of one side panel is connected to the body-facing surface of the longitudinally opposite side panel, or, alternatively, such that the clothing-facing surface of one side panel is connected to the clothing-facing surface of the longitudinally opposite side panel. Such a fin seam normally experiences a peeling stress during use of the garment. Like the embodiments illustrated in FIGS. 5-12, the resilient fastener 82 shown in FIG. 13 lies in a plane which is perpendicular to a plane in which the front panel 35 lies.

The embodiments shown in FIGS. 5-8 and 11-12 are believed to be particularly suitable for certain packaging operations, in which the prefastened, refastenable garments 20 are stacked together before placement into a container, such as a flexible bag. In these embodiments, the portions of the side panels 34/134 that are folded 180 degrees is positioned such that it is less likely to catch on, collide with, or otherwise run afoul of surrounding packaging equipment, such as manufacturing or packaging equipment or bag material.

Referring to the embodiments shown in FIGS. 5-13, the front panel 35 may have the same transverse width as the back panel 135, may be narrower than the back panel 135, or may be wider than the back panel 135. Further, the total width of the front region 22 may be the same as or different than the total width of the back region 24. For example, referring to FIGS. 2 and 3, a distance between distal edges 37 of the front side panels 34 may be equal to, greater than, or less than a distance between the distal edges 37 of the back side panels. Furthermore, the distal edges 37 of the front side panels and/or the back side panels may or may not be perpendicular to the front waist edge 38 and the back waist edge 39, respectively.

In certain embodiments, the one or more of the fastening components 82,84 may extend transversely outward past the distal edges 37 of the one or more of the side panels 34,134. "Transversely outward" refers to a direction parallel to the transverse axis 49, and away from the longitudinal midline 94 of the garment 20. For example, a fastening component 82 or 84 may attach to and extend transversely outward from a side panel 34 or 134. Alternatively, a carrier sheet, made from any suitable material, may attach to and extend transversely outward from a side panel 34,134, and a fastening component 82,84 may attach to the carrier sheet. In these ways, the orientation of the seams 80 and thus the position of the fasteners 82 of the packaged garment 20 can, in certain embodiments, be optimized. In particular embodiments, either the fastening component 82, the mating fastening component 84 (if any), or both, can be extend transversely outward past the distal edge 37 of a side panel 34 or 134.

In particular embodiments, the side panels may be selectively elasticized to assist in properly positioning the seams 80 such that the resilient fastening components lie in the proper orientation, as illustrated in FIGS. 5-13. For instance, if the front side panels 34 or the back side panels 134 are elasticized in the transverse direction, the elasticized side panels can be retracted toward the longitudinal midline 94 of the garment 20. By manipulating the amount of elasticity in the side panels 34/134, the orientation of the seams 80 and thus the position of the fasteners 82 of the packaged garment 20 can be optimized.

Another aspect of the present invention is a package 100 of prefastened, refastenable pant-like disposable garments 20, representatively illustrated in FIGS. 14-17. The package 100 includes a generally polyhedral enclosure 102 composed of a flexible polymer material surrounding a plurality of prefastened, refastenable, disposable garments 20. The enclosure includes a pair of side walls 104, a pair of end walls 106, a top wall 108, and a bottom wall 109. The plurality of garments may be assembled in any suitable manner, such as a stack 120. A description of compression packing is included in PCT WO 97/49618, published Dec. 31, 1997, the contents of which are hereby incorporated by reference.

One or more of the garments 20 in package 100 can be configured, for example, in the manner illustrated in any of FIGS. 5-13, or in any combination of the configurations representatively shown in those Figures. As illustrated, the resilient fastening components 82 of at least one prefastened garment 20 in the package 100 lies in a plane approximately perpendicular to a plane in which the front panel 35 of the garment 20 lies. In particular embodiments, such as those illustrated in FIGS. 14-16, the resilient fastening components 82 of at least one prefastened garment 20 in the package 100 lies in a plane approximately parallel to a plane in which an adjacent side wall 104 lies. In this way, the inward compressive forces associated with packaging exerted by bag side walls 104 upon the resilient fastening components 82 are unlikely to crease, deform, or otherwise damage the fastening components 82. "Adjacent" as used herein means that a component is close to or neighboring to another component, and may or may not contact to the other component.

Each package 100 contains an end garment 140. The end garment 140 is the garment positioned adjacent to an end wall 106, such that the plane in which the front or back panel of the end garment 140 lies is parallel to a plane in which the adjacent end wall 106 lies. In particular embodiments, the end garment 140 has a construction identical to the other garments 20 in the package, and accordingly includes a front region 22, a back region 24, a crotch region 26 interconnecting the front and back regions, an inner surface 28 which is configured to contact the wearer, an outer surface 30 opposite the inner surface which is configured to contact the wearer's clothing. The end garment includes two refastenable end garment seams 180, each of which includes an end garment fastening component 182, and each of which can include an end garment mating fastening component (not shown). The end garment fastening components 182 are resilient; the end garment mating fastening components, if any, may or may not be resilient.

Figure 14:
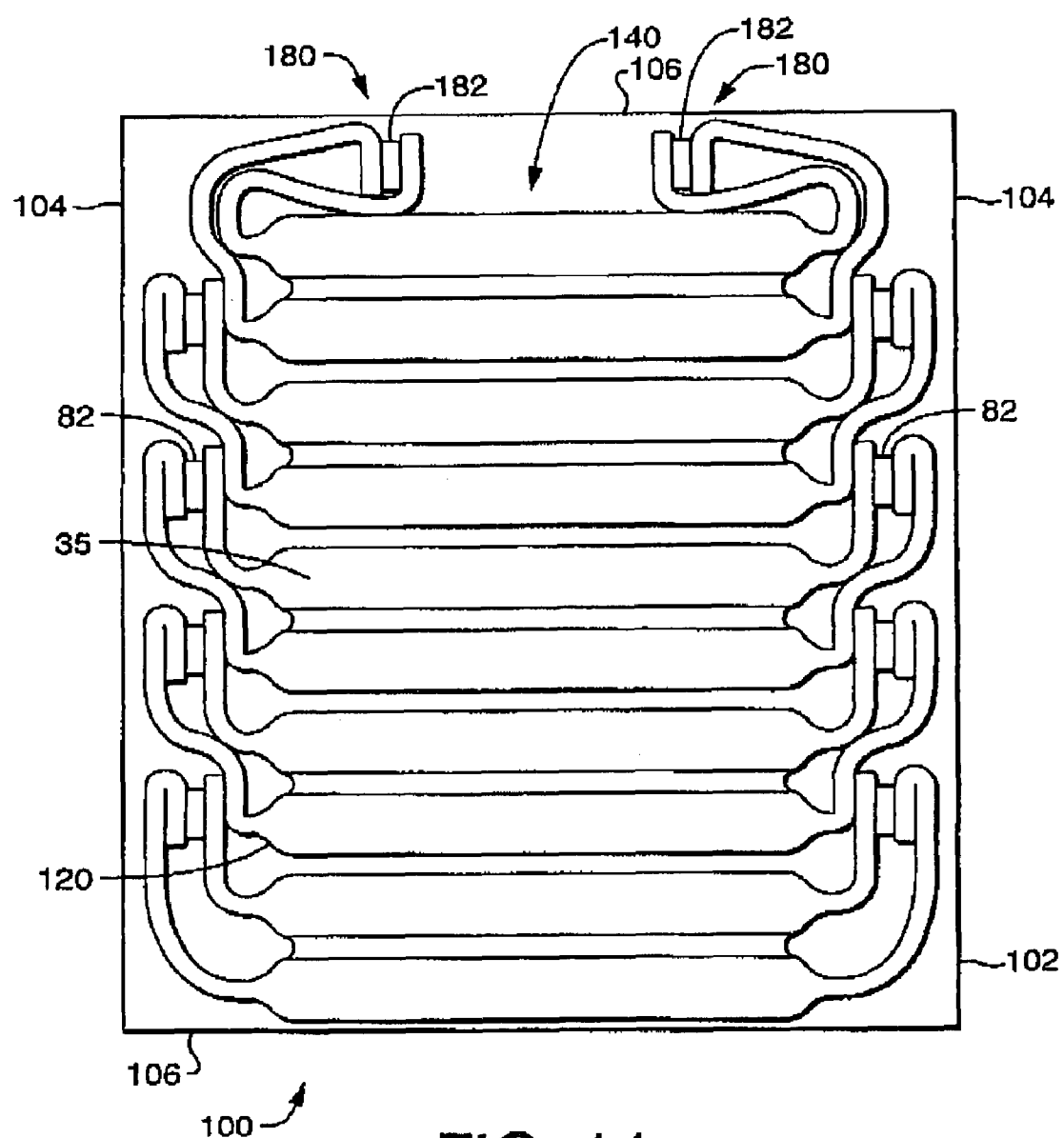
FIG. 14 is a top view of one embodiment of the package of the present invention, with the top wall omitted to show features of the garments enclosed with the package.
Figure 15:
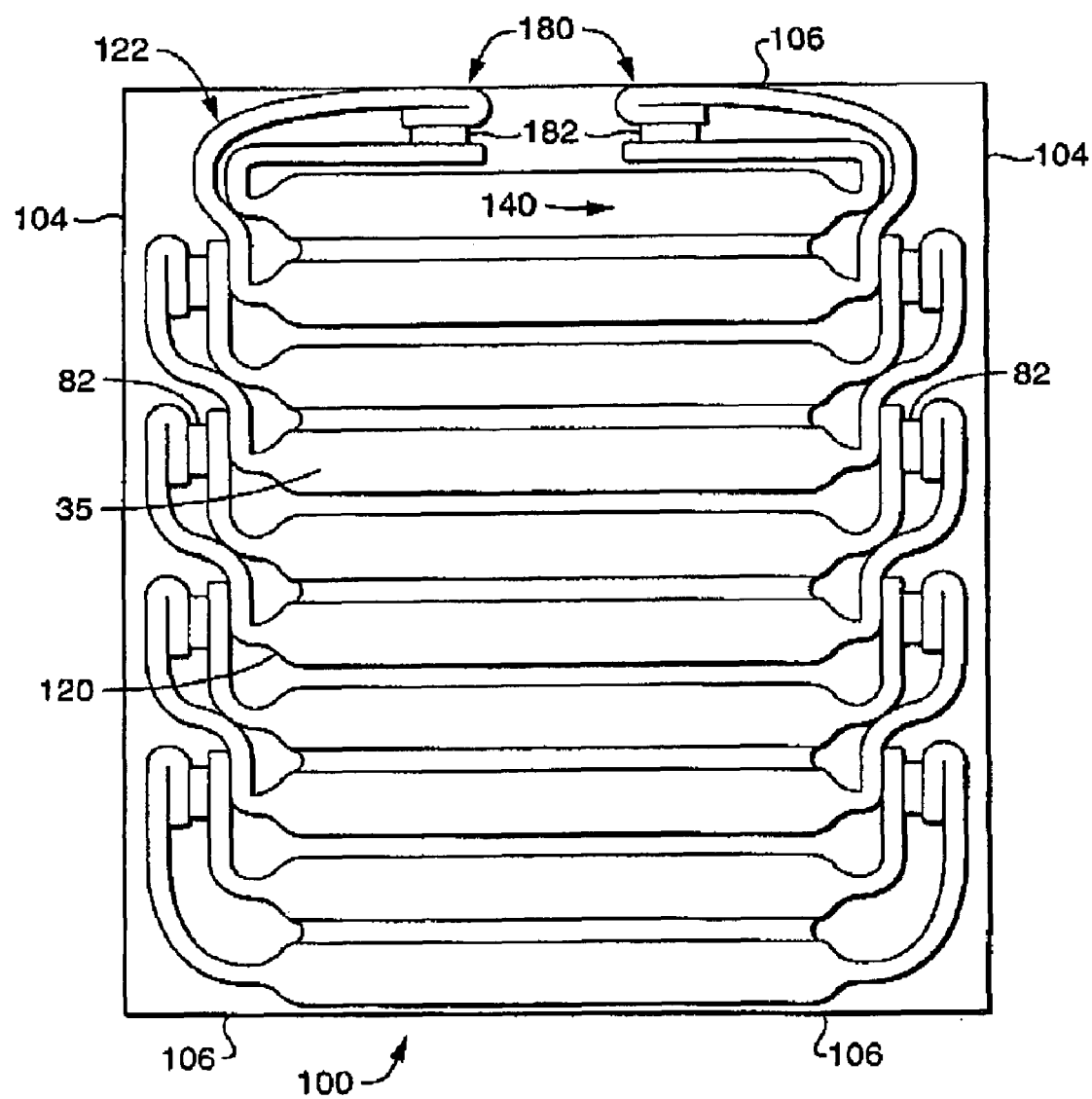
FIG. 15 is a top view of another embodiment of the package of the present invention, with the top wall omitted to show features of the garments enclosed with the package.
Figure 16:
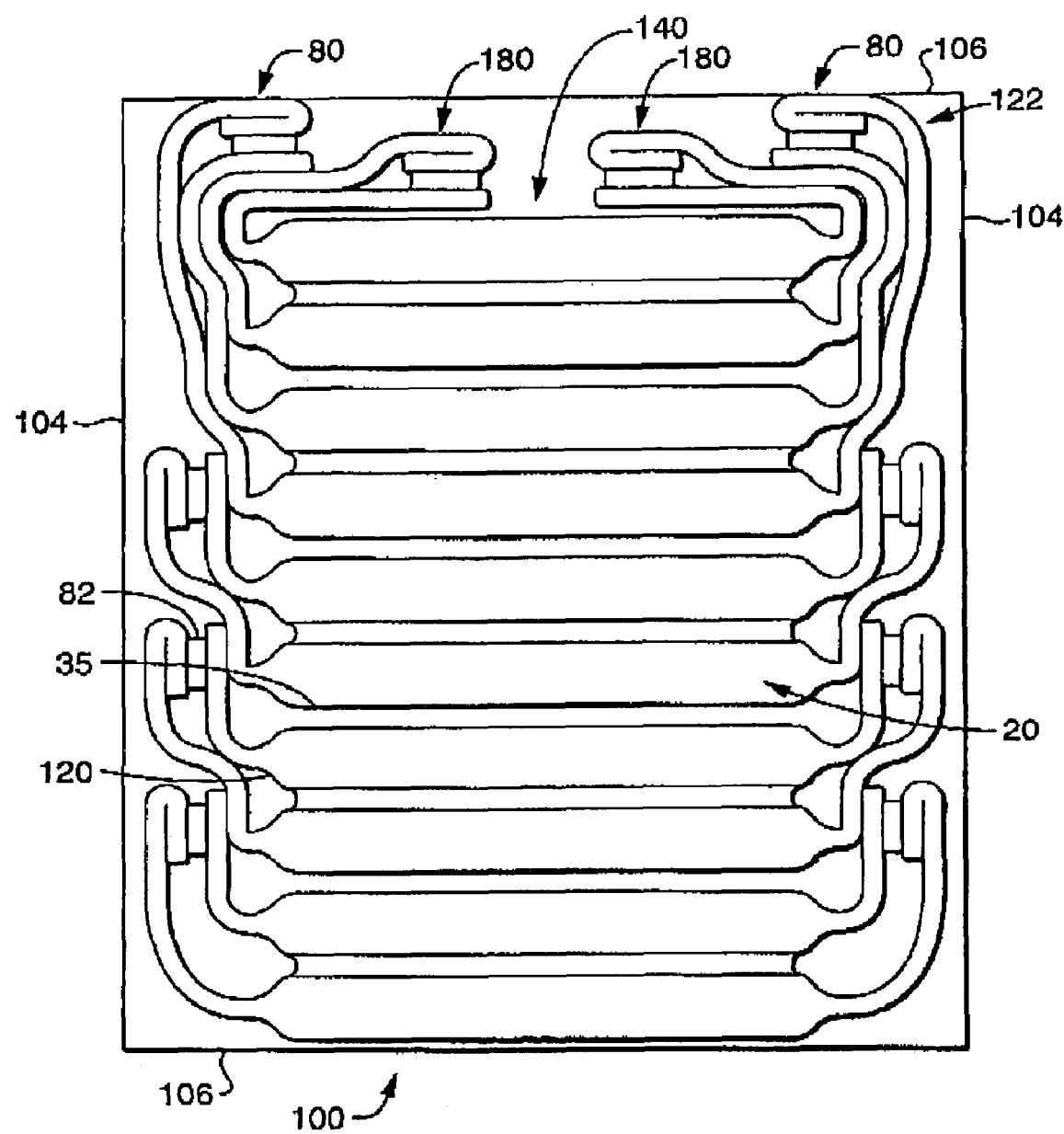
FIG. 16 a top view of another embodiment of the package of the present invention, with the top wall omitted to show features of the garments enclosed with the package.
Figure 17:
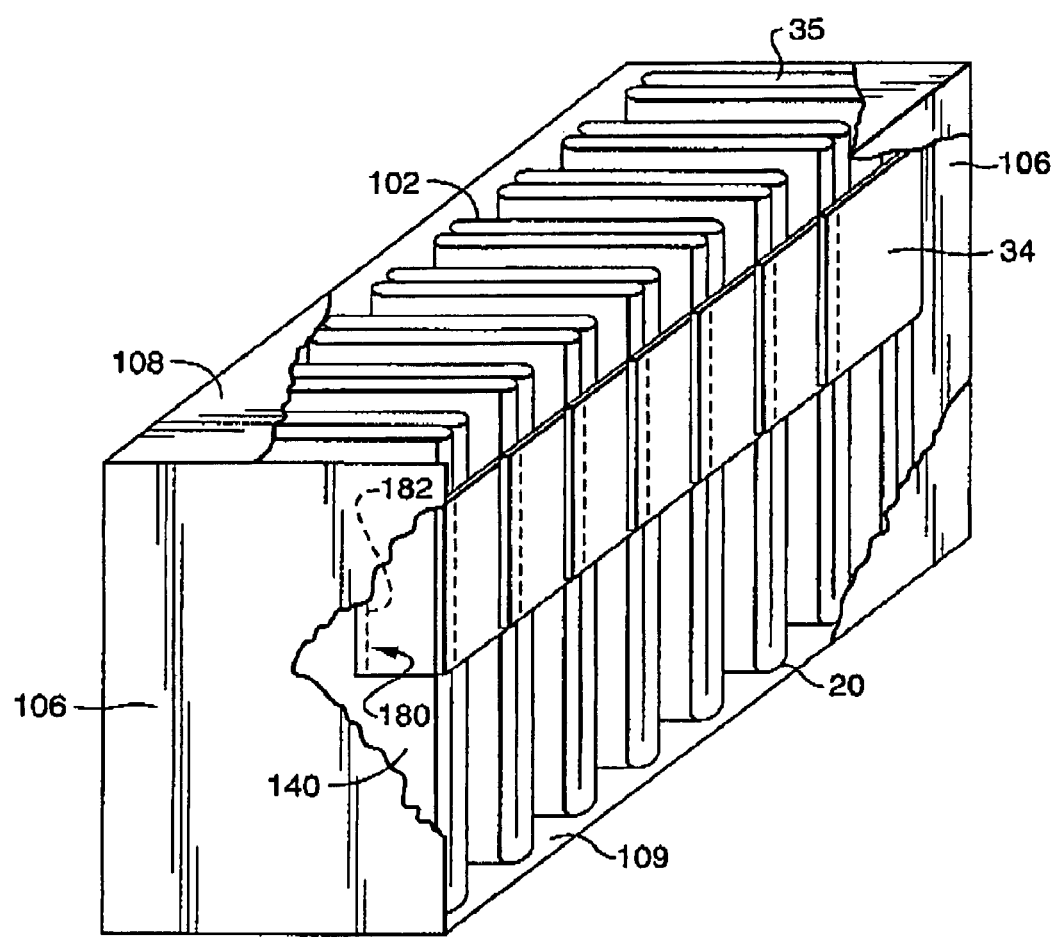
FIG. 17 is a perspective view of one embodiment of the package of the present invention, with portions cut away to show the underlying features.

When prefastened, refastenable disposable garments are packaged in the manner representatively illustrated in FIGS. 14 and 15 (i.e., with the refastenable seams 80 positioned transversely outward from the front and back panels 35 and 135, rather than being sandwiched between the front and back panels 35 and 135), an additional problem can arise. The end garment fastening components 182 can be subject to the inward compressive force of the adjacent end wall 106. If the end garment fastening components 182 are positioned in a plane perpendicular to a plane in which the adjacent end wall 106 lies, the fastening components 182 may become creased, deformed, or otherwise damaged during the packaging process (as illustrated in FIG. 14), leading to the problems previously discussed. Consequently, it is desirable in particular embodiments position the end garment fastening components 182 such that they lie in a plane parallel to a plane in which an end garment front panel 35 lies, and, in particular embodiments, in a plane parallel to a plane in which the adjacent end wall 106 of the enclosure 102 lies.

Furthermore, in particular embodiments, the end garment 140 may not be the only garment whose fastening components are subject to the inward compressive force of an end wall 104. For example, in one particular embodiment, representatively illustrated in FIG. 16, two or more prefastened, refastenable garments of the stack 120 may include refastenable seams 80 whose resilient fastening components are positioned at an end 122 of the stack 120, at least one of which is the end garment 140. In such an embodiment, both the end garment 140, and the garment adjacent the end garment, are configured within the package such that each of their resilient fastening components lie in planes approximately parallel to the plane occupied by the front panel of the end garment, and approximately parallel to the plane occupied by the adjacent end wall 106. In one particular embodiment, each resilient fastener within a package lies in a plane which is approximately parallel to the plane occupied by the enclosure wall nearest the resilient fastener. In this way, fastener damage due to the inward compressive effect which can be exerted by any particular enclosure wall can be reduced.

Note that the various components representatively illustrated in the Figures may not be drawn to scale. For example, in FIGS. 14-16, the side panels of the end garment 140 appear transversely wider than the side panels of other garments in the package 100, but the side panels of the end garment 140 can have the same transverse width as, be wider than, or be narrower than the side panels of other garments in the package 100.

Figure 18:
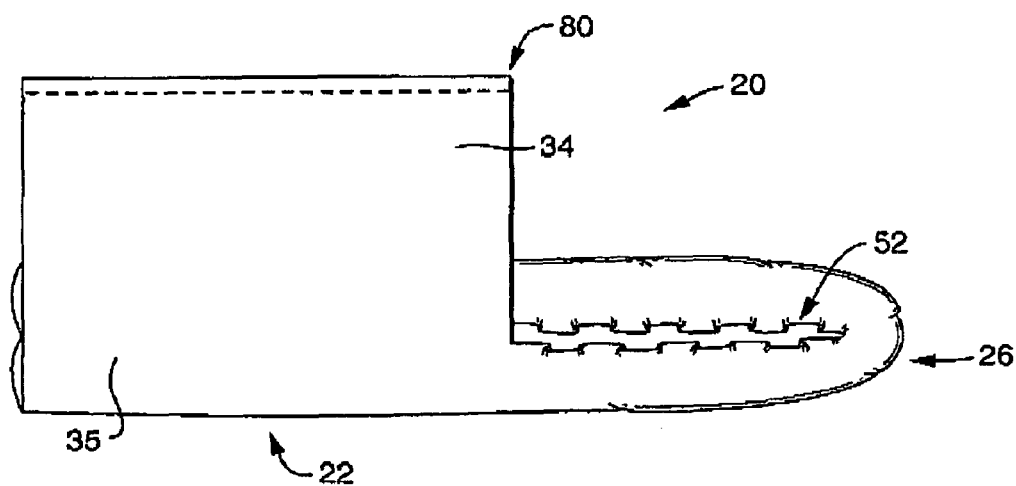
FIG. 18 is a side view of any of the disposable garments in FIGS. 5-13.
Figure 19:
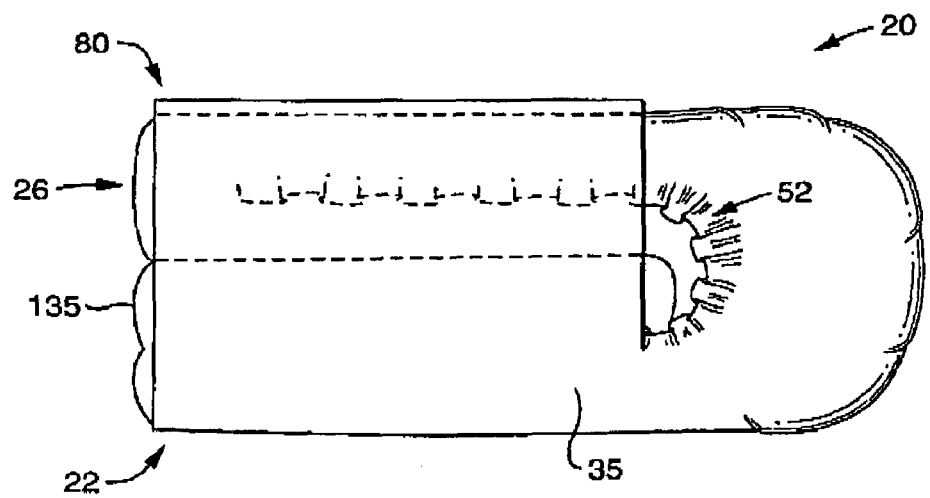
FIG. 19 is a side view of an alternative embodiment of the packaged garment of the present invention.

Each of the orientations of the refastenable seams and fastening components described above results in a garment having resilient fastening components lying in a plane such that the fastening components will not become creased during packaging. A side view representing any of the garments 20 in FIGS. 5-13 is shown in FIG. 18. Any of the configurations shown in FIGS. 5-13 can be folded once again, such that the crotch region 26 of the garment is folded onto either the front region 22 or the back region 24 of the garment, as shown in FIG. 19. When folding the garment in this manner, the fold should occur below the refastenable seam 80, such that the refastenable seam remains in a plane perpendicular to the front and back panels 35 and 135, as shown in FIG. 19. A garment having more than one fastening component 82 and/or 84 along each refastenable seam 80 can be folded between the fastening components 82 and/or 84, and may also be folded below the bottommost fastening components 82, 84.

The orientations of the refastenable seams 80 and resilient fastening components 82 of the present invention are suitable for use with garments of a wide range of sizes and proportions. For example, the orientations can be used with garments 20 having front and back panels 35, 135 of roughly equal transverse widths, or with one of the panels transversely wider than the other. Similarly, the orientations can be used with garments having front and back side panels 34, 134 of roughly equal transverse widths, or with one of the pairs of panels transversely wider than the other. Thus, the refastenable seams 80 of the invention can be located at the exact sides of the donned garment or can be skewed forward or backward from the exact sides of the donned garment. More particularly, if the front region 22 has a transverse width about equal to a transverse width of the back region 24, the refastenable seams 80 will be located at the exact sides of the donned garment 20; and if the front region 22 has a transverse width smaller than the transverse width of the back region 24, the refastenable seams 80 will be skewed forward on the garment 20; and if the front region 22 has a transverse width greater than the transverse width of the back region 24, the refastenable seams 80 will be skewed backward on the garment 20.

As mentioned, the refastenable seams 80 suitably, but need not, extend longitudinally from the waist opening 50 to the leg openings 52. The refastenable seams 80 can be any suitable transverse width and can vary greatly depending on the product. For example, each refastenable seam 80 can be in a range of about 0.25 inch to about 3.0 inches wide, more particularly about 0.5 inch to about 2.5 inches wide, or still more particularly about 0.75 inch to about 1.5 inches wide in the transverse direction.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A packaged garment defining a waist opening and a leg opening, the garment comprising,
    a front region comprising a front panel and defining a front waist edge, a back region comprising a back panel and defining a back waist edge, and a crotch region connecting the front and back regions;
    a front side panel extending transversely from a side of the front panel;
    a back side panel extending transversely from a side of the back panel;
    wherein the front side panel is connected to the back side panel to form a prefastened, refastenable seam, the refastenable seam comprising a fastening component;
    wherein the fastening component lies in a plane approximately perpendicular to a plane in which the front panel lies.

2. The garment of claim 1 wherein the refastenable seam is formed between a body-facing surface of the front side panel and a clothing-facing surface of the back side panel.

3. The garment of claim 2 wherein the front side panel is folded over a distal edge of the beck side panel.

4. The garment of claim 2 wherein the fastening component is permanently bonded to the back side panel.

5. The garment of claim 1 wherein the refastenable seam is formed between a clothing-facing surface of the front side panel and a body-facing surface of the back side panel.

6. The garment of claim 5 wherein the back side panel is folded over a distal edge of the front side panel.

7. The garment of claim 5 wherein the fastening component is permanently bonded to the front side panel.

8. The garment of claim 1 wherein the fastening component is engaged with a mating fastening component, wherein the mating fastening component is integral with a side panel.

9. The garment of claim 1 wherein the front and back side panels are bonded to the front and back panels, respectively.

10. The garment of claim 1 wherein the fastening component extends transversely outward from a side panel.

11. A packaged garment having a waist opening and two leg openings, the garment comprising:
    a front region comprising a front panel and defining a front waist edge, a back region comprising a back panel and defining a back waist edge, and a crotch region connecting the front and back regions;
    first and second front side panels extending transversely from respective aides of the front panel, each front side panel having a body facing surface and a clothing facing surface;
    first and second back aide panels extending transversely from respective aides of the back panel, each back side panel having a body facing surface and a clothing facing surface;
    wherein the first front side panel is connected to the first back side panel to form a first prefastened, refastenable seam, the first refastenable seam comprising a first fastening component;
    the second front side panel is connected to the second back side panel to form a second prefastened, refastenable seam, the second refastenable seam comprising a second fastening component;
    wherein the first and second fastening components lie in first and second planes, the first and second planes being approximately perpendicular to a plane in which the front panel lies.

12. The garment of claim 11 further wherein:
    the first and second front side panels define first and second front side panel distal edges, respectively, the first and second front side panel distal edges being approximately perpendicular to the front waist edge; and
    the first and second back side panels define first and second back side panel distal edges, respectively, the first and second back side panel distal edges being approximately perpendicular to the back waist edge,
    wherein a transverse distance between the first and second front side panel distal edges is equal to a transverse distance between the first and second back side panel distal edges.

13. The garment of claim 11, further wherein:
    the first and second front side panels define first and second front side panel distal edges, respectively, the first and second front side panel distal edges being approximately perpendicular to the front waist edge; and
    the first end second back side panels define first and second back side panel distal edges, respectively, the first and second back side panel distal edges being approximately perpendicular to the back waist edge,
    wherein a transverse distance between the first and second front side panel distal edges is less than a transverse distance between the first and second back side panel distal edges.

14. The garment of claim 11 wherein the first refastenable seam is formed between the body-facing surface of the first front side panel and the clothing-facing surface of the first back side panel, and the second refastenable seam is formed between the body-facing surface of the second front side panel and the clothing-facing surface or the second back side panel.

15. The garment of claim 14 wherein the first front side panel is folded over a distal edge of the first back side panel, and the second front side panel is folded over a distal edge of the second back side panel.

16. The garment of claim 11 wherein the first refastenable seam is formed between the clothing-facing surface of the first front side panel and the body-facing surface of the first back side panel, and the second refastenable seam is formed between the clothing-facing surface of the second front side panel and the body-facing surface of the second back side panel.

17. The garment of claim 16 wherein the first back side panel is folded over a distal edge of the first front side panel, and the second back side panel is folded over a distal edge of the second front side panel.

18. A packaged garment having a waist opening and a leg opening, the garment comprising,
   a front region comprising a front panel and defining a front waist edge, a back region comprising a back panel and defining a back waist edge, and a crotch region connecting the front and back regions;
   a front side panel extending transversely from a side of the front panel, the front side panel having a body facing surface and a clothing facing surface;
   a back side panel extending transversely from a side of the back panel, the back side panel having a body facing surface and a clothing facing surface;
   wherein the front side panel is connected to the back side panel to form a prefastened, refastenable seam, the refastenable seam comprising a fastening component,
   wherein the fastening component lies in a plane approximately parallel to a plane in which an adjacent enclosure side wall lies.

19. A package of prefastened, refastenable garments, comprising:
   a generally polyhedral enclosure composed of a flexible material surrounding a plurality of prefastened, refastenable garments, the polyhedral enclosure comprising a pair of side walls, a pair of end walls, a top wall, and a bottom wall,
   wherein each of the plurality of garments comprises:
      a front region comprising a front panel and defining a front waist edge, a back region comprising a back panel and defining a back waist edge, and a crotch region connecting the front and back regions;
      a front side panel extending transversely from a side of the front panel;
      a back side panel extending transversely from a side of the back panel;
      wherein the front side panel is connected to the back side panel to form a prefastened, refastenable seam, the refastenable seam comprising a fastening component;
   wherein the fastening component lies in a plane approximately perpendicular to a plane in which the front region lies, and in a plane approximately parallel to a plane in which an adjacent side wall lies.

20. The package of claim 19, further comprising an end garment adjacent one of the end walls, wherein the end garment comprises:
   an end garment front region comprising an end garment front panel, an end garment back region comprising an end garment back panel, and an end garment crotch region connecting the end garment front and end garment back regions;
   an end garment front side panel extending transversely from a side of the end garment front panel;
   an end garment back side panel extending transversely from a side of the end garment back panel;
   wherein the end garment front side panel is connected to the end garment back side panel to form an end garment refastenable seam, the end garment refastenable seam comprising an end garment fastening component;
   wherein the end garment fastening component lies in a plane approximately parallel to a plane in which the end garment front panel lies.

21. The package of claim 20, wherein the end garment fastening component lies in a plane approximately parallel to a plane in which an end wall adjacent to the end garment lies.

22. A package of prefastened, refastenable pant-like disposable garments, comprising:
   a generally polyhedral enclosure composed of a flexible material surrounding a plurality of prefastened, refastenable disposable garments, the polyhedral enclosure comprising a pair of side walls, a pair of end walls, a top wall, and a bottom wall, wherein each garment comprises front and back regions, a crotch region connection the front and back regions, and at a fastening component connecting the front and back regions to place each of the plurality of garments in a prefastened, pant-like configuration;
   wherein each fastening component lies in a plane which is approximately parallel to a plane occupied by an adjacent enclosure wall.

* * * * *